(12) United States Patent
Mogna

(10) Patent No.: US 10,413,576 B2
(45) Date of Patent: Sep. 17, 2019

(54) THERAPY FOR USE IN THE TREATMENT OF TUMORS, ACQUIRED IMMUNODEFICIENCY SYNDROME AND LEUKEMIAS BY DUAL IMMUNE BIOSTIMULATION

(71) Applicant: Giovanni Mogna, Novara (IT)

(72) Inventor: Giovanni Mogna, Novara (IT)

(73) Assignee: Giovanni Mogna, Novara (IT)

( * ) Notice: Subject to any disclaimer, the term of this patent is extended or adjusted under 35 U.S.C. 154(b) by 0 days.

(21) Appl. No.: 15/307,756

(22) PCT Filed: Apr. 30, 2015

(86) PCT No.: PCT/IB2015/000602
§ 371 (c)(1),
(2) Date: Oct. 28, 2016

(87) PCT Pub. No.: WO2015/170158
PCT Pub. Date: Nov. 12, 2015

(65) Prior Publication Data
US 2017/0042951 A1    Feb. 16, 2017

(30) Foreign Application Priority Data

May 5, 2014 (IT) .............................. MI2014A0816

(51) Int. Cl.
| | | |
|---|---|---|
| A61K 35/747 | (2015.01) | |
| A61K 35/74 | (2015.01) | |
| A61K 35/745 | (2015.01) | |
| A61K 36/886 | (2006.01) | |
| A61K 35/00 | (2006.01) | |

(52) U.S. Cl.
CPC ............ *A61K 35/747* (2013.01); *A61K 35/74* (2013.01); *A61K 35/745* (2013.01); *A61K 36/886* (2013.01); *A61K 2035/115* (2013.01)

(58) Field of Classification Search
CPC .. A61K 35/747; A61K 36/886; A61K 35/745; A61K 35/74; A61K 2035/115
See application file for complete search history.

(56) References Cited

U.S. PATENT DOCUMENTS

| | | | |
|---|---|---|---|
| 6,103,227 A | 8/2000 | Wolf et al. | |
| 2009/0274672 A1 | 11/2009 | Yu et al. | |
| 2010/0143305 A1 | 6/2010 | Lemke | |
| 2010/0203018 A1 | 8/2010 | Benedetti et al. | |
| 2013/0309212 A1 | 11/2013 | Zhang et al. | |
| 2017/0112883 A1 | 4/2017 | Mogna | |

FOREIGN PATENT DOCUMENTS

| | | |
|---|---|---|
| JP | 2007084533 A | 4/2007 |
| JP | 2009269906 A | 11/2009 |
| JP | 2010534470 A | 11/2010 |
| KR | 20100049827 A | 5/2010 |
| KR | 20130048946 A | 5/2013 |
| WO | 2009/013709 A2 | 1/2009 |
| WO | 2012/143787 A1 | 10/2012 |
| WO | 2013034974 A1 | 3/2013 |
| WO | 2013/114185 A1 | 8/2013 |
| WO | 2015/170158 A1 | 11/2015 |
| WO | 2015/170159 A1 | 11/2015 |

OTHER PUBLICATIONS

International Search Report and Written Opinion for International Application No. PCT/IB2015/000602 filed Apr. 30, 2015 on behalf of Giovanni Mogna, dated Aug. 17, 2015. 11 pages.
WPI/Thomson Scientific; Database "XP002728393 & KR20100049827A" May 13, 2010. 2 pages.
WPI/Thomson Scientific; Database "XP002728394 & KR20130048946A" May 13, 2013. 2 pages.
International Preliminary Report on Patentability for International Application No. PCT/IB2015/000602 filed on Apr. 30, 2015 on behalf of Giovanni Mogna, dated Nov. 8, 2016 7 pages.
International Preliminary Report on Patentability for International Application No. PCT/IB2015/000614 filed on Apr. 30, 2015 on behalf of Giovanni Mogna, dated Nov. 8, 2016 7 pages.
International Search Report for International Application No. PCT/IB2015/000614 filed on Apr. 30, 2016 on behalf of Giovanni Mogna, dated Jul. 1, 2015 4 pages.
Non-Final Office Application for U.S. Appl. No. 15/307,757, filed on Oct. 28, 2016, on behalf of Hoffmann-Eitle SRL, dated Oct. 10, 2018. 11 pgs.
Restriction Requirement for U.S. Appl. No. 15/307,757 filed on Oct. 28, 2016 on behalf Giovanni Mogna, dated Feb. 16, 2018 7 pages.
Written Opinion for International Application No. PCT/IB2015/000614 filed on Apr. 30, 2015 on behalf of Giovanni Mogna, dated Jul. 1, 2015 6 pages.
Iyer C. et al., "Probiotic Lactobacillus reuteri promotes TNF-induced apoptosis in human myeloid leukemia-derived cells by modulation of NF-kB and MAPK signaling" Cellular Microbiology Mar. 26, 2008 12 pages.
Office Action for Japanese Application No. 2016-566657 dated May 14, 2019 7 pages (English Summary + Original).
The Journal of the Japanese Association for Infectious Diseases, vol. 62, No. 12, P1105- 1110, 1988, (Japanese Only).
Wolf W. et al., "Safety and Tolerance of Lactobacillus reuteri supplementation to a Population Infected with the Human Immunodeficiency Virus" *Food and Chemical Toxicology* 1998 11 pages.
Yagi A. et al., "Bioactive ingredients of Aloe: a review update" Fukuyama University 2002 28 pages (English Abstract + Original).

(Continued)

*Primary Examiner* — Kade Ariani
(74) *Attorney, Agent, or Firm* — Steinfl + Bruno, LLP

(57) ABSTRACT

A composition for human and animal use as a therapy for the treatment of tumors, acquired immunodeficiency syndrome and leukemias is described. The composition, for human and animal use as an antitumor agent, has a strain of bacteria *Lactobacillus reuteri* LRE 03 DSM 23879 which is able to strongly stimulate the production of pro-inflammatory cytokines (Th1) interferon INF-gamma, the cytokines exhibiting a marked antitumor activity, and/or a strain of bacteria *Lactobacillus salivarius* LSO6 DSM 26037 which is able to strongly stimulate the production of dendritic cells, the dendritic cells also exhibiting a marked antitumor activity.

17 Claims, 6 Drawing Sheets

THERAPY FOR USE IN THE TREATMENT OF TUMORS, ACQUIRED IMMUNODEFICIENCY SYNDROME AND LEUKEMIAS BY DUAL IMMUNE BIOSTIMULATION

CROSS-REFERENCE TO RELATED APPLICATIONS

The present application is the U.S. National Stage of International Patent Application No. PCT/IB2015/000602 filed on Apr. 30, 2015, the corrected version of which was published on Nov. 12, 2015, which, in turn, claims priority to Italian Application No. MI2014A000816 filed on May 5, 2014.

The present invention relates to a composition for human and animal use as a therapy for the treatment of tumors, acquired immunodeficiency syndrome and leukemias. The composition of the present invention, for human and animal use as antitumor agent, comprises a mixture comprising or, preferably, consisting of a strain of bacteria *Lactobacillus reuteri* LRE 03 DSM 23879 which is able to strongly stimulate the production of pro-inflammatory cytokines (Th1) interferon INF-gamma, said cytokines exhibit a marked antitumor activity, and/or a strain of bacteria *Lactobacillus salivarius* LS06 DSM 26037 which is able to strongly stimulate the production of dendritic cells, said dendritic cells also exhibit a marked antitumor activity.

As regards oncology, the current medical therapy is known to comprise chemotherapy, endocrine therapy, the treatment with immune response modifiers and the treatment with molecular-targeted drugs. The main purpose of antitumor chemotherapy is to kill, at any cell cycle phases, neoplastic cells and thus, reduce both primary tumor and metastasis masses.

It is known that antitumor chemotherapeutic treatments decrease the immune system activity and that a compromised immune system is unable to protect organisms against viral and bacterial infections.

In addition, it is known that chemotherapy (chemo) primarily affects the tumor but, unfortunately, it also causes side-effects on healthy tissues, specifically those with a fast proliferation and turnover, such as esophageal, gastric and intestinal mucosae, resulting in mucositis, nausea, vomiting, diarrhea, nutrient malabsorption and, thus, malnutrition.

Therefore, the common denominator of all chemotherapeutics is: bone marrow toxicity, which, in turn, leads to immunodepression and consequent infections, mainly caused by Gram-negative bacteria and fungi such as *Candida*, gastrointestinal epithelium toxicity and intestinal microflora toxicity (chemotherapeutic antibiotics).

Accordingly, it would be desirable to have a natural, effective and well-tolerated composition so that to lessen the adverse effects, typical of a chemotherapeutic treatment.

Thus, there is still a strong need for having an adjunctive therapy in order to prevent and/or reduce both symptoms and side effects of chemotherapy being used for the treatment of tumors.

Furthermore, there is still a need for having an adjunctive therapy to chemotherapy, being able to act on immune system by stimulating it (immunostimulation), in order to restore its efficacy, since chemotherapy is well known to entail a reduction of the immune system efficacy.

Figure 1:
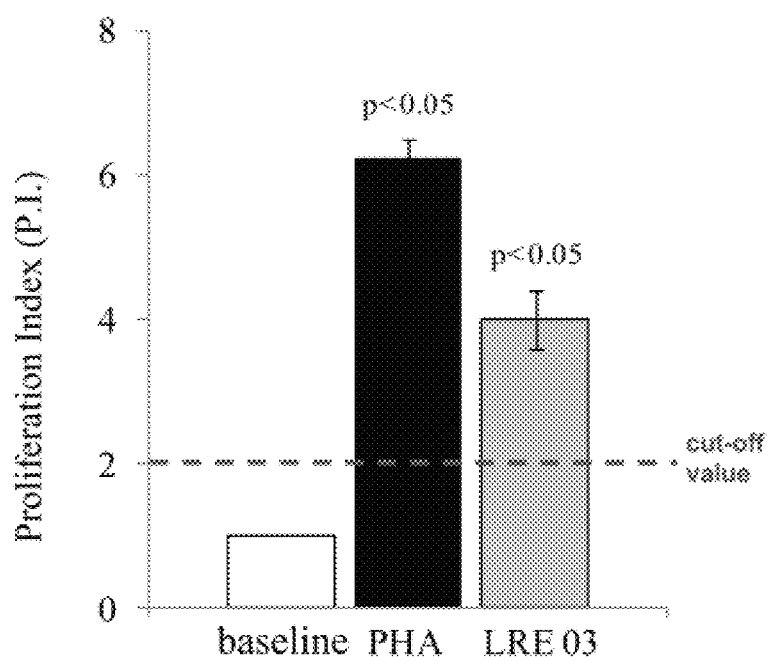
FIG. 1 shows a plot reporting the cell proliferation index (P.I.) of PHA and LRE 03 in comparison to the baseline. The PBMC proliferative response under all the stimulation conditions resulted significantly higher than in absence of stimulation (baseline).

After a long and intensive research and development activity on a wide group of bacterial strains belonging to different species, the Applicant identified and selected specific bacterial strains, which suitably meet the above-cited needs.

It is an object of the present invention:
a strain of bacteria belonging to the species *Lactobacillus reuteri* identified as *Lactobacillus reuteri* LRE03 with deposit number DSM 23879, deposited on May 08, 2010 by Probiotical SpA at DSMZ—Deutsche Sammlung von Mikroorganismen und Zellkulturen GmbH, under the Budapest Treaty, and/or
a strain of bacteria belonging to the species *Lactobacillus salivarius* identified as *Lactobacillus salivarius* LS06 with deposit number DSM 26037, deposited on Jun. 06, 2012 by Probiotical SpA at DSMZ—Deutsche Sammlung von Mikroorganismen und Zelikulturen GmbH, under the Budapest Treaty.

The Applicant found that the strain of bacteria *Lactobacillus reuteri* LRE03 DSM 23879 shows a proven and surprising ability (see experimental part) to stimulate the production of pro-inflammatory cytokines (Th1) interferon INF-gamma. The strain of bacteria *Lactobacillus reuteri* LRE03 DSM 23879 shows a surprising immunostimulatory activity towards the endogenous production of interferon gamma IFN-gamma. The strain of bacteria *Lactobacillus reuteri* LRE03 DSM 23879, selected by the Applicant, exhibits a surprising immunomodulatory activity, since it activates the immune system through the stimulation of pro-inflammatory cytokines (Th1) interferon INF-gamma. The endogenous cytokine stimulation/production does not cause toxicity, as opposed to the infusion administration of said cytokines, as in the case of exogenous cytokines.

By virtue of the strong stimulation of the production of pro-inflammatory cytokines (Th1) interferon INF-gamma, the strain of bacteria *Lactobacillus reuteri* LRE03 DSM 23879 is able to exert an effective antitumor action, by counteracting and reducing tumor cell proliferation.

The Applicant also found that the strain of bacteria *Lactobacillus salivarius* LSO6 DSM 26037 exhibits a proven and surprising ability (see experimental part) to stimulate the dendritic cell production. Dendritic cells assist the immune system in protecting organisms from outside attacks of dangerous microorganisms, such as viruses and bacteria.

Because of its strong stimulation of dendritic cell production, the strain of bacteria *Lactobacillus salivarius* LS06 DSM 26037 is able to exert an effective antitumor action, by counteracting and reducing tumor cell proliferation.

It is an object of the present invention a (i) mixture of bacteria comprising or, alternatively, consisting of: a strain of bacteria *Lactobacillus reuteri* LRE03 DSM 23879, and/or a strain of bacteria *Lactobacillus salivarius* LS06 DSM 26037, for human or animal use as antitumor agent.

In an embodiment, said mixture (i) comprises or, alternatively, consists of:
a strain of bacteria *Lactobacillus reuteri* LRE03 DSM 23879, and/or
a strain of bacteria *Lactobacillus salivarius* LS06 DSM 26037, for human or animal use in tumor treatment for counteracting and/or reducing tumor cell proliferation, in acquired immunodeficiency syndrome treatment and leukemia treatment.

In another embodiment, the (i) mixture of bacteria comprises or, alternatively, consists of:
a strain of bacteria *Lactobacillus reuteri* LRE03 DSM 23879 and a strain of bacteria *Lactobacillus salivarius* LS06 DSM 26037, in a weight ratio comprised from 1:5 to 5:1, preferably from 1:3 to 3:1, even more preferably from 1:2 to 2:1 or 1:1.

The (i) mixture of bacteria has a bacterial cell concentration comprised from $1 \times 10^8$ UFC/g of mixture to $1 \times 10^{12}$ UFC/g of mixture, preferably from $1 \times 10^9$ UFC/g of mixture to $1 \times 10^{11}$ UFC/g of mixture. Within the context of the present invention, all the above-cited mixtures are referred to, for the sake of brevity, as "the mixture of bacteria or the mixtures of bacteria of the present invention".

It is another object of the present invention a pharmaceutical composition or a medical device composition, which is meant as a substance in compliance with the directive 93/42/EEC definition, hereinafter referred to, for the sake of brevity, as "the composition or compositions of the present invention", said composition comprises or, alternatively, consists of:
(i) a mixture of bacteria of the present invention, as described above, and/or
(ii) a mixture comprising or, alternatively, consisting of a gum, preferably an alginate or a derivative thereof, and/or a gel, preferably an Aloe gel or a derivative thereof, and/or
(iii) a source of highly assimilable zinc, and/or
(iv) one or more food grade or pharma grade excipients and/or additives and/or co-formulants, acceptable by the body, such as preferably fructooligosaccharides (FOS), green tea, sucralose and/or maltodextrins.

In an embodiment, which is an object of the present invention, the composition of the present invention comprises or, alternatively, consists of: (i) a mixture of bacteria of the present invention and (iv) one or more food grade or pharma grade excipients and/or additives and/or co-formulants, acceptable by the body, said composition being for human and animal use in antitumor chemotherapeutic treatments, acquired immunodeficiency syndrome treatments and leukemia treatments.

In another embodiment, which is an object of the present invention, the composition of the present invention comprises or, alternatively, consists of: (i) a mixture of bacteria of the present invention, (ii) a mixture comprising or, alternatively, consisting of a gel, preferably an *Aloe* gel or a derivative thereof and (iv) one or more food grade or pharma grade excipients and/or additives and/or co-formulants, acceptable by the body, said composition being for human and animal use in antitumor chemotherapeutic treatments, acquired immunodeficiency syndrome treatments and leukemia treatments. Said (ii) mixture comprises or, alternatively, consists of a gel, preferably an *Aloe* gel or a derivative thereof. The Aloe product, or a derivative thereof, is preferably *Aloe arborescens*; preferably in freeze-dried form. *Aloe arborescens* is preferably in freeze-dried form and exerts an anti-inflammatory action.

Furthermore, the Applicant found that the immune system (IS) activation by the composition of the present invention takes place through a "dual biostimulation". The "dual biostimulation" consists of a first and a second biostimulations. The first biostimulation is obtained due to the presence, in the composition of the present invention, of very highly bioavailable zinc. This biologically available form of zinc stimulates the thymus to producing a greater amount (number) of lymphocytes. Said T-lymphocytes "overproduced" by the thymus produce non-toxic endogenous cytokines, such as interferon-gamma and dendritic cells.

The second biostimulation, combined with the first one, is promoted by the strain of bacteria *Lactobacillus reuteri* LRE03 DSM 23879 and/or the strain of bacteria *Lactobacillus salivarius* LS06 DSM 26037 which, in turn, stimulate lymphocytes, now in a greater amount due to the previous thymus stimulation by the zinc, to producing more cytokines (specifically, INF-gamma and dendritic cells). In addition to the above, there is also a basal anti-inflammatory effect ensured by the presence of Aloe or a derivative thereof, preferably *Aloe arborescens*; preferably in freeze-dried form.

The very high bioavailability of zinc derives from the fact that it is in the form of zinc internalized inside a tyndallized bacterial cell of a bacterial strain belonging to the species *Bifidobacterium lactis*, preferably the strain selected by the Applicant is the strain of bacteria *Bifidobacterium lactis* Bb 1 DSM 17850 deposited at DSMZ on Dec. 23, 2005, being the object of the European Patent Application No. 08789404, herein incorporated by reference.

Basically, the Applicant found that the highly bioavailable zinc internalized into a tyndalized cell (inactivated cell) is able to activate the immune system (IS), specifically the thymus responsible for the production of T-lymphocytes, which produce non-toxic endogenous cytokines, such as interferon-gamma and dendritic In another embodiment, which is an object of the present invention, the composition of the present invention comprises or, alternatively, consists of: (i) a mixture of the present invention, (ii) a mixture comprising or, alternatively, consisting of a gel, preferably an *Aloe* gel or a derivative thereof, (iii) a source of highly assimilable and bioavailable zinc in the form of zinc internalized inside a tyndallized bacterial cell of a strain of bacteria belonging to the species *Bifidobacterium lactis*, preferably said strain is the strain of bacteria *Bifidobacterium lactis* Bb 1 DSM 17850 and (iv) one or more food grade or pharma grade additives and/or co-formulants and/or formulation technological ingredients, acceptable by the body, said composition being for human and animal use in antitumor chemotherapeutic treatments, acquired immunodeficiency syndrome treatments and leukemia treatments. Said (iv) source of highly assimilable and bioavailable zinc is present as organic zinc in the form of bacterial tyndallized product of the strain *Bifidobacterium lactis* Bb1 DSM 17850 (ProbioZinc®, deposited on Dec. 23, 2005 at DSMZ—Deutsche Sammlung von Mikroorganismen und Zelikulturen GmbH, by BioMan S.r.l. Company (Italy). The tyndallized bacterial product of the strain *Bifidobacterium animalis* ssp. *lactis* Bb1 DSM 17850 is in an amount comprised from 10 to 50 mg/g of composition, preferably 20 mg/g of composition.

All the above-cited compositions of the present invention are effectively applicable for use as adjunctive therapy to antitumor chemotherapeutic treatments, acquired immunodeficiency syndrome treatments and leukemia treatments.

Finally, the composition of the present invention comprises food grade or pharma grade excipients and/or additives and/or co-formulants, which allow the manufacture of pharmaceutical forms as powders, granules, tablets or capsules. It can also contain, for example, fructooligosaccharides FOS and/or green tea and/or sucralose and/or maltodextrins.

The composition of the present invention comprises from $1 \times 10^8$ to $1 \times 10^{12}$ of viable bacterial cells UFC/g of composition, preferably from $1 \times 10^9$ to $1 \times 10^{11}$ of viable bacterial cells UFC/g of composition. The composition of the present invention is preferably recommended to be administered 1-2 times daily for 4-12 weeks.

The composition of the present invention comprises said *Aloe*, advantageously freeze-dried *Aloe* arborescens in an amount comprised from 1 to 25% by weight, relative to the weight of the composition; preferably from 5 to 15% by weight, relative to the weight of the composition. The composition of the present invention may contain freeze-dried *Aloe arborescens* (AlageI™) for example 1.5 gram/dose. in light of its overall mechanism of action, the composition of the present invention is able to make the side effects of a chemotherapeutic treatment more tolerable in individuals with a tumor disease.

In an embodiment, the composition of the present invention comprises the (i) mixture of the present invention (having a bacterial cell concentration comprised from $1 \times 10^8$ UFC/g of mixture to $1 \times 10^{12}$ UFC/g of mixture, preferably from $1 \times 10^9$ UFC/g of mixture to $1 \times 10^{11}$ UFC/g of mixture) comprising or, alternatively, consisting of:
  a strain of bacteria *Lactobacillus reuteri* LRE03 DSM 23879, or
  a strain of bacteria *Lactobacillus salivarius* LS06 DSM 26037, or
  a strain of bacteria *Lactobacillus reuteri* LRE03 DSM 23879 and a strain of bacteria Lactobacillus salivarius LS06 DSM 26037, in a weight ratio comprised from 1:5 to 5:1, preferably from 1:3 to 3:1, even more preferably from 1:2 to 2:1 or 1.1, and/or fructooligosaccharides FOS and/or green tea and/or sucralose and/or maltodextrins.

Indeed, the strain *L. reuteri* LRE03 DSM 23879 is able to significantly stimulate the endogenous production of interferon-gamma (IFN-γ). The ability of the strain *L. reuteri* LRE03 DSM 23879 to induce the release of cytokines, in particular interferon-gamma INF-gamma, by the primary cells of immune system was quantified by co-incubation thereof with PBMCs (Peripheral Blood Mononuclear Cells) isolated from peripheral blood of healthy adult individuals. The results showed a stimulation of IFN-gamma secretion with a concentration of 480 pg/ml, namely 47-fold greater than the control. The IFN-gamma production was assessed in the culture supernatant after 5 days of stimulation relative to non-stimulation conditions (baseline). Interferon-gamma (IFN-γ) has hindrance properties against viral and bacterial infections, similarly to the other interferons, and non-physiological cell proliferation, which is mediated by changes of cytoskeleton and cell membrane, modulations of oncogene product expression and regulation of the cell differentiation process (protraction of almost all the phases of mitosis both in normal and tumor cells). IFNI-γ also shows a pivotal and characteristic immunornodulatory effect, by stimulating the activity of both cells specialized in the body's immune response such as macrophages, monocytes, neutrophils and unspeciaiized cells such as platelets, endothelial and epithelial cells, fibroblasts and parenchymal cells. The composition of the present invention ensures a suitable amount (2 mg/dose) of highly assimilable zinc internalized by the microorganism *Bifidobacterium lactis* Bb1. The highly bioavailable (internalized) zinc is in the form of a tyndallized (inactivated) cell. This form of zinc is very bioavailable and, thus, more easily assimilable by the organism. The zinc ion, being bioavailable and readily assimilable by the organism, plays a pivotal role and a direct action towards the thymus, which is responsible for the stimulation/production of lymphocytes, which produce more cytokines.

The strain of bacteria *Bifidobacterium lactis* Bb 1 DSM 17850 was deposited at DSMZ on 23.12.2005, by BioMan S.r.l. Company (Italy). Indeed, the strain of bacteria *Bifidobacterium lactis* Bb 1 DSM 17850 is able to accumulate zinc inside the cell during its growth in a liquid culture medium, The dietary zinc accumulated inside the cell (ProbioZinc®) has an assimilability 17-fold greater than zinc gluconate and 31.5-fold greater than zinc sulfate, as shown in an in vitro study carried out on Caco-2 cells in a Transwell system. The high assimilability of the trace element zinc allows to effectively counterbalancing deficiency conditions even at very low dosages. Furthermore, zinc is known for playing an important role on the immune system, specially the thymus, the organ where the production of T-lymphocytes takes place which, when differentiate to CD4+ T-lymphocytes (helper T-lymphocytes), secrete a series of cytokines such as IL-12 and IFN-γ. Said zinc mechanism of action is synergistic with that of the strain *L. reuteri* LRE03 DSM 23879.

In light of its overall mechanism of action, the composition being object of the present invention is effectively applied for use as adjunctive therapy in individuals with tumor diseases and undergoing chemotherapy, as well as in antiretroviral treatments in individuals with Acquired Immunodeficiency Syndrome (AIDS) and leukemia treatments.

EXPERIMENTAL PART

The Applicant tested the immunomodulatory properties of the strain of bacteria *Lactobacillus reuteri* LRE 03 (ID1777) DSM 23879, as described below.

Specifically, the investigation was conducted after different times of stimulation, so that to analyze both cytokines involved in innate immunity and those responsible for acquired immunity.
a) Bacterial Cultures and Growth Conditions Firstly, bacterial cultures of the strain of bacteria *Lactobacillus reuteri* LRE 03 DSM 23879 were prepared under specific growth conditions. The strain was cultured in Man Rogosa Sharpe (MRS) medium, in a thermostatic bath at 37° C. As regards the immunomodulatory experiments, after a growth period of approximately 16 hours, bacteria were subcultured for 6 hours, under the above-cited conditions, in order to reach the exponential growth phase. Then, they were washed twice with sterile phosphate-buffered saline (PBS, pH 7.2); the physiological status and the number of cells were determined with a cytofluorimetric technique by using the commercial kit "Cell Viability Kit with liquid beads", marketed by Becton Dickinson Company, following the manufacturer's instructions. The cells were thus brought to the optimal concentration established in preliminary experiments and used in subsequent tests.

b) Peripheral Blood Mononuclear Cell Separation

Next, peripheral blood mononuclear cells were separated. The peripheral blood mononuclear cells (PBMC) were separated by density gradient centrifugation. For this aim, 20 ml of "buffy coat" of healthy donors from the immune-transfusion Service of Ospedale di Borgomanero (Italy) were used for each experiment, thus obtaining an average yield of $200 \times 10^6$ PBMC/buffy. The amount of separated cells was determined by cell count in Burker's chambers, using Turk's dye, which allows to discriminating between mononuclear and polymorphonuclear cells. Cells were brought to a concentration of $2 \times 10^6$ cells/nil in RPMI-1640 growth medium (invitrogen), supplemented with 10% heat inactivated Bovine fetal serum (FCS, Gibco), 1% glutamine and 25 mM Hepes.

c) PBMC Stimulation

Next, the peripheral blood mononuclear cells (PBMC) were stimulated with the bacterial strain. After separation, PBMCs were stimulated with the bacterial strain for 1 and 5 days. The internal controls for each experiment were as follows:

Negative control: PBMCs alone 1 day control: PBMCs stimulated with 1 µg/ml Lipopolysaccharide (LPS; *Escherichia coil*, serotype 055:B5, Sigma Chemicals Co., St, Louis, Mo.), 5 days control; PBMCs stimulated with 1 µg/ml Phytohaernaggiutinin (PHA-P; Sigma Chemicals Co., St. Louis, Mo.).

At the different times of analysis, cultures were centrifuged at 1500 rpm for 10 minutes. Supernatants were taken and stored at $-20°$ C. until analysis. The cells were used for subsequent tests.

d) Cell Proliferation Analysis

Then, the cell proliferation analysis was performed. Cell proliferation was assessed with a cytofluorimetric technique by using the bromodeoxyuridine (BrdU) nuclear labeling protocol. This method was developed as alternative to the more traditional radiolabeling system with tritiated thymidine. Particularly, cell cultures were added with a mixture of 5-bromo-2'-deoxyuridine (BrdU) and 2'-deoxycytidine (do), either at 20 µM final concentration. Following to 16-hour incubation at 37° C. under humidified atmosphere, 5% $CO_2$, the cell proliferation was analyzed by a cytofluorimetric technique. The culture supernatants were harvested and stored at $-20°$ C. until analysis. Following to fixation and cell wall permeabilization, the cellular DNA was labeled with anti-BrdU FITC-conjugated monoclonal antibody (mAb) (Becton Dickinson). The cells were analyzed within 24 hours from their preparation by using a cytofluorimeter FACScalibur from Becton Dikinson Company and the analysis program CellQuest.

Results were expressed as cell proliferation index (P.I.), being calculated as ratio of the percentage of proliferating cells in the presence of stimulus and the percentage of the same in the absence of stimulation, A P.I. value greater than 2 was considered acceptable (cut-off value). In all the experiments, stimulation with the mitogen (PHA) as control always resulted greater than the cut-off value, confirming that PBMCs were viable and with proliferative capability.

e) Analysis of Molecules Characterizing Individual Cell Subpopulations

Next, the analyses of molecules characterizing the individual cell subpopulations were performed. As regards the immunophenotypic characterization, the cells were incubated for 30 minutes in the dark, with different combinations of the following monoclonal antibodies (mAb) conjugated to fluorescein isothiocyanate (FITC), phycoerythrin (PE) or peridinin chlorophyll protein (PerCP): CD3, CD4, CD8, CD14, CD16, CD19, CD20, 0D56, HLA-DR. After incubation, the samples were washed, fixed with a solution containing 1% paraformaldehyde and stored at 4'C. Within 24 hours from preparation, the samples were analyzed by a cytofluorimeter FACScalibur, the cells being selected so that to exclude contaminant cellular debris from analysis.

f) Cytokine Dosage

Next, the cytokine dosage was performed. Cytokine concentration in the culture supernatants was determined by E.L.I.S.A., assay (Enzyme-Linked Immunoabsorbent Assay). Specifically, for cytokine (IL-4, IL-10, IFN-γ and IL-12p70) dosage, the kits "Human ELISA Ready-SET-Go" from eBioscence Company, San Diego Calif. were used:

g) Statistical Analysis

A statistical analysis by using the paired Student's t test was performed. A $p<0.05$ value was considered significant.

Results i) The proliferative response induced by the strain of bacteria *Lactobacillus reuteri* LRE 03 DSM 23879 was determined. In vitro analysis of cell proliferation is a very useful biological parameter for investigating the immune system functioning. In order to analyze whether the tested bacterial strain could affect the induction of lymphocyte proliferation, peripheral blood mononuclear cells (PBMC) were stimulated with the bacterial strain *Lactobacillus reuteri* LRE 03 DSM 23879. Phytohaemagglutinin (PHA), which is a mitogenic stimulus able to induce T-Iymphocyte polyclonal proliferation, was used as positive control. PBMCs were separated from peripheral venous blood samples of 4 healthy male donors, average age of 40 years (range 21-52 years), from the Transfusion Service of Ospedale S. S. Trinità, Borgomanero (Novara).

As shown in FIG. 1, where the cell proliferation index (P.I., see the above-described methods) is reported, the PBMC proliferative response under all the stimulation conditions resulted significantly higher than in absence of stimulation (baseline).

In FIG. 1, the Mean ± standard error of the mean (S.E.M.) of 4 independent experiments is shown. The statistical significance was calculated by using the Student's t test. $p<0.05$ values have to be considered statistically significant, as compared to the baseline (non-stimulated PBMCs).

ii) The effects of the bacterial strain *Lactobacillus reuteri* LRE 03 DSM 23879 on the different cell subpopulations were assessed. in order to detect which cell subpopulations were induced to proliferate following to stimulation with the tested probiotic strain, a multiparametric flow cytometry analysis was performed. The subsequent figures (FIG. 2 and FIG. 3) show the percentage of the main cell subpopulations involved both in natural and acquired immune response.

iia) Natural Immunity. After one day, the stimulation with the bacterial strain *Lactobacillus reuteri* LRE 03 (DSM 23879) caused a change in total dendritic cell (Lineage-/HLA-DR+) percentage.

Figure 2:
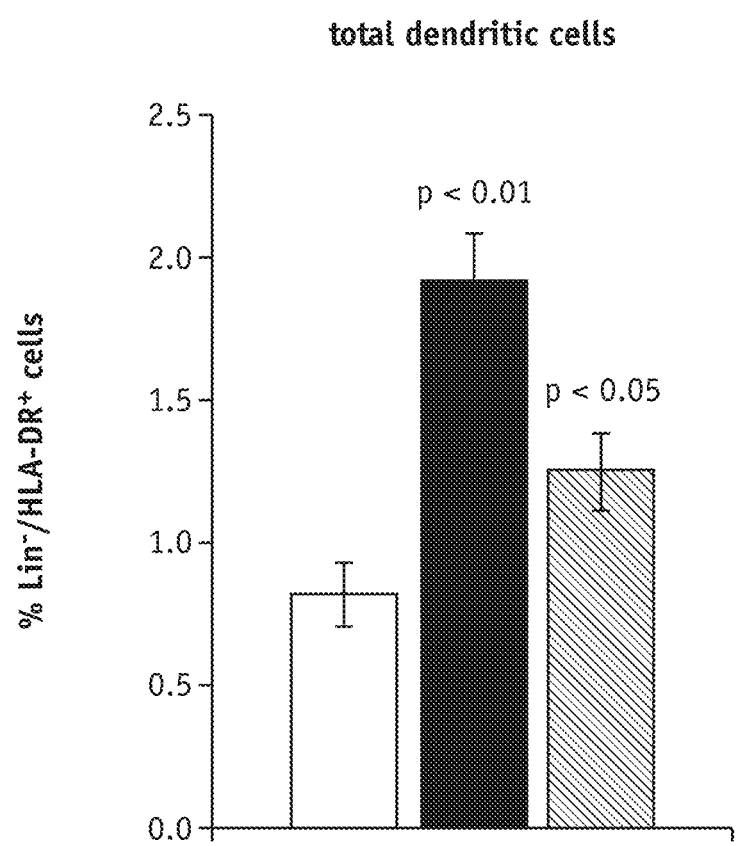
FIG. 2 shows a plot reporting the percentage of total dendritic cell in PHA and LRE 03 relative to the baseline.

In FIG. 2, the proliferative response Mean±S.E.M. of 4 independent experiments is shown. The statistical significance was calculated by using the Student's t test. $p<0.05$ values have to be considered statistically significant, as compared to the baseline (non-stimulated PBMCs).

iib) Acquired Immunity. After five days, the stimulation with the bacterial strain *Lactobacillus reuteri* LRE 03 DSM 23879 caused a significant increase in helper T-lymphocytes (CD3+/CD4) percentage.

Figure 3:
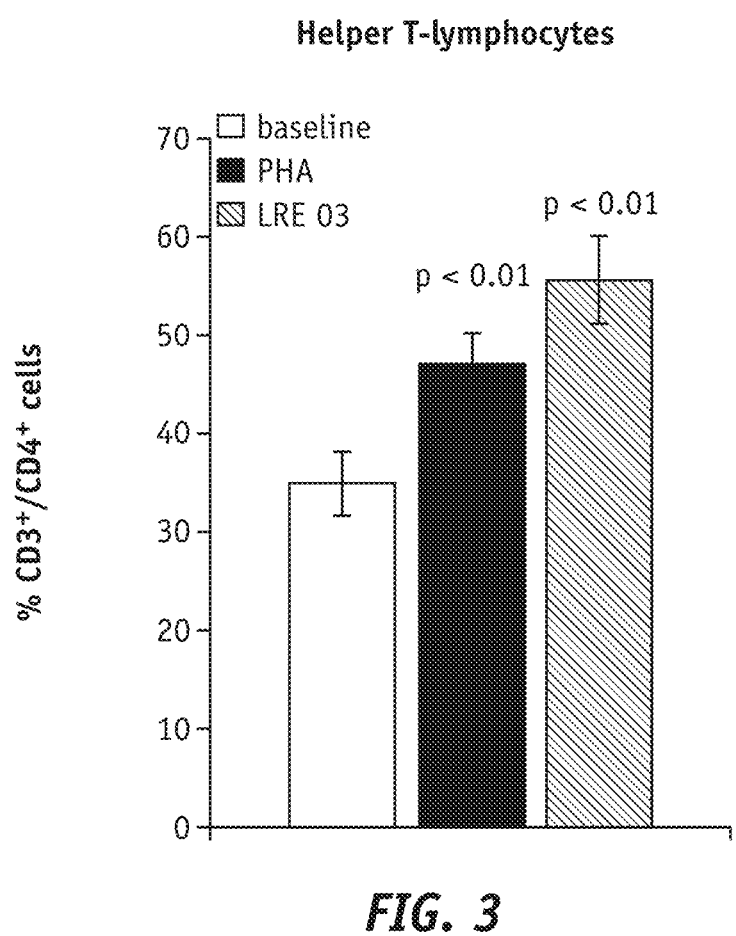
FIG. 3 shows a plot reporting the percentage of helper T-lymphocytes in PHA and LRE 03 relative to the baseline.
Figure 4:
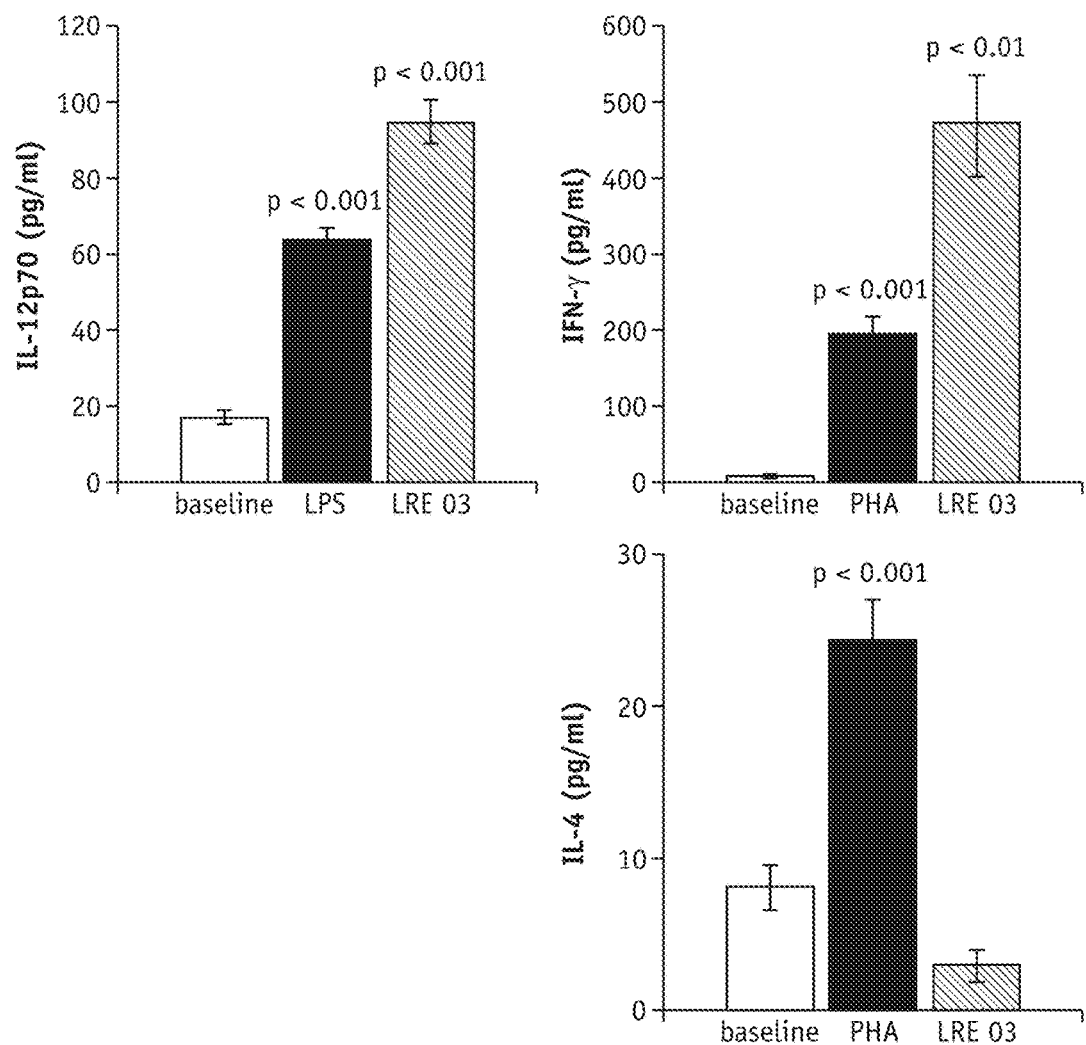
FIG. 4 shows three plot reporting the amount of cytokine IL-12p70, IFN-γ and IL-4 being released in PHA, LPS and LRE 03 relative to the baseline.

In FIG. 3, the Mean ± S.E.M. of 12 independent experiments is shown. The statistical significance was calculated by using the Student's t test. p<0.05 values have to be considered statistically significant, as compared to the basal condition (non-stimulated PBMCs).

iii) Cytokine secretion. The different spectrum of cytokines secreted by cell subpopulations involved in immune responses plays a pivotal role in selecting the effector system to be used in response to a specific antigenic stimulus. T-lymphocytes represent the main effector and regulatory cells of cell-mediate immunity. In response to an antigen or pathogenic agent, T-cells synthetize and secrete a variety of cytokines required for growth and differentiation and as activating factors of other immunocompetent cells. In order to investigate whether the tested bacterial strain would induce a different cytokine secretion by PBMCs, said cells were activated for 1 and 5 days. The amount of cytokines (IL-12p70, IFN-γ and IL-4) being released in the culture supernatants was measured by E.L.I.S.A. assay.

iv) Cytokines with predominantly pro-inflammatory action. The induction of cytokines IL-12p70 and IFN-γ, as main representatives of cytokines with predominantly pro-inflammatory action was assessed. As shown in FIG. 4, the bacterial strain *Lactobacillus reuteri* LRE 03 (DSM 23879) is able to induce a significant increase of both the tested cytokines, relative to basal conditions.

v) Cytokines with predominantly immunoregulatory action. The induction of cytokines IL-4, as main representatives of cytokines with predominantly immunoregulatory action was assessed. As shown in FIG. 4, the tested bacterial strain *Lactobacillus reuteri* LRE 03 (DSM 23879) shown to be able to induce a reduction of cytokine IL-4 secretion, relative to basal conditions.

In FIG. 4 the Mean±S.E.M. of 4 independent experiments is shown. The statistical significance was calculated by using the Student's t test, p<0.05 values have to be considered statistically significant, as compared to the baseline (non-stimulated PBMCs). The production of cytokines IL-12p70 was assessed in culture supernatants after 1 day of stimulation. IFN-γ and IL-4 production was assessed in culture supernatants after 5 days of stimulation.

Figure 5:
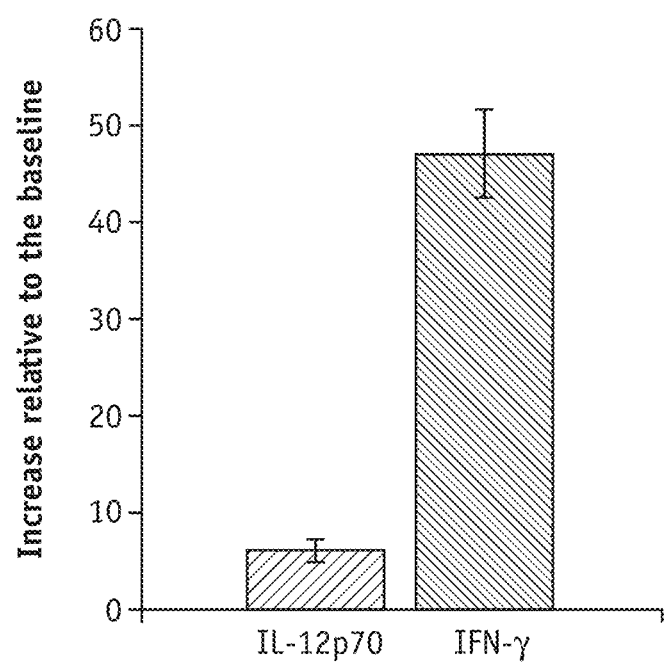
FIG. 5 shows a plot reporting the increase relative to the baseline by LRE 03 strain. The bacterial strain *Lactobacilus reuteri* LRE 03 DSM 23879 increased by 6-fold and 47-fold the secretion of cytokine IL-12p70 and cytokine IFN-γ respectively relative to non-stimulation conditions.

Data relative to the dosage of cytokines secreted by PBMCs following to stimulation with the bacterial strain *Lactobacillus reuteri* LRE 03 DSM 23879 underlined the capability of the strain itself to significantly increase pro-inflammatory cytokines. Specifically, the bacterial strain *Lactobacillus retiteri* LRE 03 DSM 23879 increased by 6-fold and 47-fold the secretion of cytokine IL-12p70 and cytokine IFN-γ, respectively, relative to non-stimulation conditions (baseline, FIG. 5).

Considering the marked ability of the bacterial strain *Lactobacillus reuteri* LRE 03 DSM 23879 to stimulate the cytokine IFN-γ secretion, the results of the present study were compared to those obtained from experiments with other bacterial strains, all belonging to Probiotical S.p.A. collection. Specifically, the increase relative to the baseline was compared, namely the fold change of the IFN-γ amount, relative to non-stimulation conditions (baseline).

As shown in table 1, the bacterial strain *Lactobacillus reuteri* LRE 03 (DSM 23879) resulted the best IFN-γ inducing agent relative to both strains of the same species and strains of different species, all belonging to the genus *Lactobacillus*.

In Table 1, the increase of cytokine IFN-γ induced by stimulation with different lactobacilli and bifidobacteria, compared to the baseline, is shown.

EXPERIMENTAL PART

The Applicant tested the immunomodulatory properties of the bacterial strain *Lactobacillus salivarius* LS 06 DSM 26037, as described below.

Specifically, the immunomodulatory properties towards total circulating dendritic cells of the probiotic strain *Lactobacillus salivarius* LS 06 DSM 26037, previously characterized from both the microbiological and molecular point of views, were assessed. In particular, after 24 hours of stimulation, a multiparametric flow cytometry analysis, by selecting the DCs in peripheral blood mononuclear cells from healthy adults donors, was carried out.

a) Bacterial Cultures and Growth Conditions

The strain was cultured in Man Rogosa Sharpe (MRS) medium, in a thermostatic bath at 37° C. As regards the immunomodulatory experiments, following to a growth period of approximately 16 hours, the bacteria were subcultured for 6 hours, under the above-cited conditions, in order to reach the exponential growth phase. Thus, they were washed twice with sterile phosphate-buffered saline (PBS, pH 7.2); the physiological status and the number of cells were determined with a cytofluorimetric technique by using the commercial kit "Cell Mobility Kit with liquid beads", marketed by Becton Dickinson Company, following the manufacturer's instructions. The cells were then brought to the optimal concentration established in preliminary experiments and used in subsequent tests.

b) Peripheral Blood Mononuclear Cell Separation

Peripheral blood mononuclear cons (PBMC) were separated by density gradient centrifugation. For this aim, 20 ml of "buffy coat" of healthy donors from the Immuno-transfusion Service of Ospedale di Borgomanero were used for each experiment, thereby obtaining an average yield of $200 \times 10^6$ PBMC/buffy, The amount of separated cells was determined by cell count in Burker's chambers, by using Turk's dye, which allows to discriminating between mononuclear cells and polymorphonuclear cells. The cells were brought to a concentration of $2 \times 10^6$ cells/ml in RPMI-1640 growth medium (lnvitrogen), supplemented with 10% heat inactivated Bovine fetal serum (FCS, Gibco), 1% glutamine and 25 mM Hepes.

c) PBMC Stimulation

After separation, PBMCs were stimulated for 24 hours with the bacterial strain. The internal controls for each experiment were as follows: Negative control: PBMCs alone; 1 day control: PBMCs stimulated with 1 μg/ml Lipopolysaccharide (LPS; *Escherichia coil*, serotype 055: B5, Sigma Chemicals Co., St. Louis, Mo.).

After stimulation, the cultures were centrifuged at 1500 rpm for 10 minutes. Then the supernatant was discharged and the cells used for subsequent tests.

d) Total Dendritic Cells Analysis

As regards the immunophenotypic characterization, cells were incubated for 30 minutes in the dark with different combinations of the following monoclonal antibodies (rnAb) conjugated to fluorescein isothiocyanate (FITC) or peridinin chlorophyll protein (PerCP): CD3, CD14, CD16, CD19, CD20, CD56 and HLA-DR. After incubation, the samples were washed, fixed with a solution containing 1% paraformaidehyde and stored at 4° C. Within 24 hours from preparation, the samples were analyzed by a cytofluorimeter FACScalibur, the cells being selected so that to exclude contaminant cellular debris from analysis.

e) Statistical Analysis

A statistical analysis by using the paired Student's f test was performed. A p<0.05 value was considered significant.

Results: Bacterial Strain Effect on Dendritic Cells

In order to determine the effect of the tested probiotic strain to the dendritic cell modulation, a multiparametric flow cytometric analysis was carried out.

Figure 6:
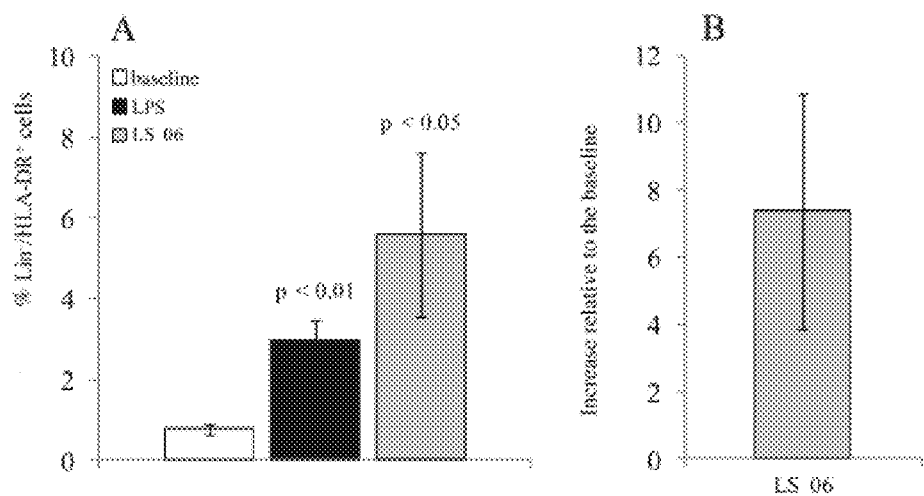
FIG. 6 shows two plots reporting in panel A the increase of total dendritic cell (Lineage-/HLA-DR+) percentage induced by the strain LS 06 compared to the baseline and LPS and in panel B the increase relative to the baseline by LS 06. In particular the bacterial strain *L. salivarius* LS 06 (DSM 26037) increased by 7-fold the percentage of total dendritic cells relative to non-stimulation conditions (baseline) (panel B).

As shown in FIG. 6, panel A, after 24 hours, the stimulation with the strain LS 06 induced a significant increase of total dendritic cell (Lineage-/HLA-DR+) percentage.

Specifically, the bacterial strain *L. salivarius* LS 06 (DSM 26037) increased by 7-fold the percentage of total dendritic cells, relative to non-stimulation conditions (baseline, FIG. 6, panel B).

In FIG. 6, panel B, the Mean±S.E.M. of 12 independent experiments is shown. The statistical significance was calculated by using the Student's t test. $p<0.05$ values have to be considered statistically significant, as compared to the baseline (non-stimulated PBMCs).

In Table 2, the increase of dendritic cells induced by stimulation with different lactobacilli and bifidobacteria, relative to the baseline, is shown.

Conclusions

Data demonstrated that the bacterial strain *L. salivarius* LS 06 induced a significant increase of total DC percentage, relative to the standard basal conditions. In particular, the bacterium LS 06 increased by 7-fold the total DC percentage.

The intestinal colonization by bacteria capable to modulating the dendritic cells, such as the strain *L. salivarius* LS 06 being characterized in the present study, is a very important factor in diseases characterized by an immunological imbalance.

TABLE 1

| Single strains | Abbreviation | ID | Deposit No. | No. of individuals | IFN-g |
|---|---|---|---|---|---|
| *L. casei* subsp. *paracasei* | LPC 08 | 1696 | DSM 21718 | 8 | 7.83 ± 0.56 |
| *L. fermentum* | LF 11 | 1639 | DSM 19188 | 8 | 8.67 ± 1.06 |
| *L. paracasei* | LPC 00 | 1076 | LMG P-21380 | 8 | 7.83 ± 0.56 |
| *L. paracasei* | LPC 00 | 1076 | LMG P-21380 | 4 | 8.06 ± 0.95 |
| *L. plantarum* | LP 09 | 1837 | DSM 25710 | 4 | 22.29 ± 4.09 |
| *L. pentosus* | LPS 01 | 1702 | DSM 21980 | 8 | 19.54 ± 1.68 |
| *L. reuteri* | LRE 01 | 1775 | DSM 23877 | 4 | 2.79 ± 0.61 |
| *L. reuteri* | LRE 03 | 1777 | DSM 23879 | 4 | 47.02 ± 4.38 |
| *L. rhamnosus* | LR 05 | 1602 | DSM 19739 | 10 | 4.16 ± 1.06 |
| *L. salivarius* | LS 06 (L166) | 1727 | DSM 26037 | 4 | 4.95 ± 0.92 |
| *L. salivarius* | DL V8 | 1813 | DSM 25545 | 4 | 2.74 ± 0.57 |
| *B. animalis* subsp *lactis* | BS 01 | 1195 | LMG P-21384 | 10 | 6.84 ± 0.81 |
| *Bifidobacterium longum* | DL BL07 | 1820 | DSM 25669 | 4 | 15.25 ± 4.01 |
| *Bifidobacterium longum* | DL BL08 | 1823 | DSM 25670 | 4 | 8.95 ± 1.77 |
| *Bifidobacterium longum* | DL BL09 | 1821 | DSM 25671 | 4 | 12.01 ± 2.75 |
| *Bifidobacterium longum* | DL BL10 | 1824 | DSM 25672 | 4 | 11.35 ± 2.09 |
| *Bifidobacterium longum* | DL BL11 | 1825 | DSM 25673 | 4 | 11.85 ± 3.78 |
| *Bifidobacterium longum* | BL01 | 1239 | None | 4 | 21.9 ± 4.67 |
| *Bifidobacterium longum* | BL02 | 1295 | None | 4 | 20.84 ± 0.89 |
| *Bifidobacterium longum* | BL03 | 1152 | DSM 16603 | 4 | 24.44 ± 5.45 |
| *Bifidobacterium longum* | BL04 | 1740 | DSM 23233 | 4 | 19.11 ± 5.38 |
| *Bifidobacterium longum* | W11 | 1114 | None | 4 | 26.01 ± 7.40 |
| *Bifidobacterium longum* | W11 wt | 1161 | None | 4 | 27.42 ± 6.78 |
| *Bifidobacterium longum* | PCB133 | 1687 | DSM 24691 | 4 | 29.09 ± 8.25 |
| *Bifidobacterium longum* | BL05 | 1352 | DSM 23234 | 4 | 14.94 ± 2.28 |
| *Bifidobacterium longum* | BL06 | no ID | DSM 24689 | 4 | 31.90 ± 3.96 |
| *L. acidophilus* | LA02 | 1688 | DSM 21717 | 8 | 4.91 ± 0.70 |
| *L. deldrueckii* subsp. *delbrueckii* | LDD01 | 1391 | DSM 22106 | 8 | 6.46 ± 0.92 |
| *L. fermentum* | LF09 | 1462 | DSM 18298 | 8 | 0.80 ± 0.15 |
| *L. fermentum* | LF10 | 1637 | DSM 19187 | 8 | 4.25 ± 0.4 |
| *L. plantarum* | LP01 | 1171 | LMG P-21021 | 8 | 1.77 ± 0.42 |
| *L. plantarum* | LP02 | 91 | LMG P-21020 | 8 | 4.59 ± 0.59 |
| *L. reuteri* | LRE02 | 1774 | DSM 23878 | 4 | 1.19 ± 0.12 |
| *L. reuteri* | LRE04 | 1779 | DSM 23880 | 4 | 1.72 ± 0.39 |
| *L. reuteri* | DLLRE07 | — | DSM 25683 | 4 | 1.00 ± 0.07 |
| *L. reuteri* | DLLRE08 | 1841 | DSM 25684 | 4 | 0.93 ± 0.06 |
| *L. reuteri* | DLLRE09 | 1842 | DSM 25685 | 4 | 1.22 ± 0.29 |
| *L. rhamnosus* | LR06 | 1697 | DSM 21981 | 10 | 2.64 ± 0.83 |
| *L. salivarius* | LS01 | 1797 | DSM 22775 | 10 | 1.44 ± 0.13 |
| *L. salivarius* | LS04 | — | DSM 24618 | | |
| *L. salivarius* | LS03 | 1382 | DSM 22776 | 10 | 0.72 ± 0.26 |
| *L. salivarius* | DLV1 | 1806 | DSM 25138 | 8 | 1.40 ± 0.13 |
| *L. salivarius* | LS05 (L66) | 1719 | DSM 26036 | 4 | 1.80 ± 0.09 |
| *L. salivarius* | LS02 | 1468 | DSM 20555 | 8 | 1.32 ± 0.67 |
| *B. lactis* | BA05 | 1518 | DSM 18352 | 8 | 1.24 ± 0.08 |
| *B. breve* | BR03 | 1270 | DSM 16604 | 10 | 2.20 ± 0.20 |
| *B. breve* | BR03 | 1270 | DSM 16604 | 8 | 6.92 ± 1.02 |
| *B. pseudolongum* subsp. *globosum* | BPS01 | 1812 | None | 8 | 0.64 ± 0.33 |
| *B. longum* | B1975 | 1742 | DSM 24709 | 4 | 2.99 ± 0.71 |

TABLE 2

| Single strains | Abbreviation | ID | Deposit No. | No. of individuals | Dendritic cells |
|---|---|---|---|---|---|
| L. fermentum | LF 11 | 1639 | DSM 19188 | 8 | 0.98 ± 0.12 |
| L. paracasei | LPC 00 | 1076 | LMG P-21380 | 8 | 1.47 ± 0.24 |
| L. pentosus | LPS 01 | 1702 | DSM 21980 | 8 | 1.46 ± 0.28 |
| L. reuteri | LRE 03 | 1777 | DSM 23879 | 4 | 2.11 ± 0.59 |
| L. rhamnosus | LR 05 | 1602 | DSM 19739 | 10 | 1.84 ± 0.29 |
| L. salivarius | LS06 (L166) | 1727 | DSM 26037 | 4 | 7.35 ± 3.52 |
| B. animalis subsp. lactis | BS 01 | 1195 | LMG P-21384 | 10 | 1.32 ± 0.12 |
| L. acidophilus | LA02 | 1688 | DSM 21717 | 8 | 0.76 ± 0.16 |
| L. deldrueckii subsp. Delbrueckii | LDD01 | 1391 | DSM 22106 | 8 | 1.14 ± 0.19 |
| L. fermentum | LF09 | 1462 | DSM 18298 | 8 | 1.23 ± 0.12 |
| L. fermentum | LF10 | 1637 | DSM 19187 | 8 | 1.03 ± 0.19 |
| L. plantarum | LP01 | 1171 | LMG P-21021 | 8 | 0.86 ± 0.18 |
| L. plantarum | LP02 | 91 | LMG P-21020 | 8 | 1.27 ± 0.18 |
| L. salivarius | LS01 | 1797 | DSM 22775 | 10 | 3.93 ± 2.01 |
| L. salivarius | LS04 | — | DSM 24618 | | |
| L. salivarius | LS03 | 1382 | DSM 22776 | 10 | 5.96 ± 3.53 |
| L. salivarius | LS02 | 1468 | DSM 20555 | 8 | 3.97 ± 1.80 |
| B. lactis | BA05 | 1518 | DSM 18352 | 8 | 1.34 ± 0.47 |
| B. breve | BR03 | 1270 | DSM 16604 | 10 | 1.83 ± 0.29 |

The invention claimed is:

1. A method to provide an adjunctive therapy to an individual undergoing antitumor chemotherapeutic treatment, acquired immunodeficiency syndrome treatment or leukemia treatment, the method comprising:
administering to the individual a composition comprising
a strain of bacteria *Lactobacillus reuteri* LRE03 with deposit number DSM 23879, deposited on May 8, 2010 by Probiotical SpA at DSMZ—Deutsche Sammlung von Mikroorganismen und Zellkulturen GmbH, and/or
a strain of bacteria *Lactobacillus salivarius* LS06 with deposit number DSM 26037, deposited on Jun. 6, 2012 by Probiotical SpA at DSMZ—Deutsche Sammlung von Mikroorganismen und Zellkulturen GmbH,
thereby providing adjunctive therapy to said individual undergoing antitumor chemotherapeutic treatment, acquired immunodeficiency syndrome treatment or leukemia treatment.

2. The method according to claim 1, wherein said composition has a bacterial concentration from $1 \times 10^8$ UFC/g to $1 \times 10^{12}$ UFC/g.

3. The method according to claim 1, wherein said composition comprises
a strain of bacteria *Lactobacillus reuteri* LRE03 DSM 23879 and a strain of bacteria *Lactobacillus salivarius* LS06 DSM 26037, in a weight ratio from 1:5 to 5:1.

4. The method according to claim 1, wherein said composition further comprises an *Aloe* gel or a derivative thereof.

5. The method according to claim 1, wherein said composition further comprises a freeze-dried *Aloe arborescens* in an amount from 1 to 25% by weight, relative to the weight of the composition.

6. The method according to claim 1, wherein said composition further comprises a tyndallized bacterial product of *Bifidobacterium lactis* Bb 1 with deposit number DSM 17850, deposited at DSMZ on 23 Dec. 2005, by BioMan S.r.l. Company.

7. The method according to claim 6, wherein said tyndallized bacterial product is in an amount from 10 to 50 mg/g of composition.

8. The method according to claim 1, wherein said composition further comprises one or more food grade excipients, or pharma grade excipients, and/or additives acceptable by the body, and/or a co-formulant acceptable by the body.

9. The method according to claim 1, wherein said composition has a bacterial concentration from $1 \times 10^9$ UFC/g to $1 \times 10^{11}$ UFC/g to treat tumors in human and animal.

10. The method according to claim 1, wherein said composition comprises a strain of bacteria *Lactobacillus reuteri* LRE03 DSM 23879 and a strain of bacteria *Lactobacillus salivarius* LS06 DSM 26037, in a weight ratio from 1:3 to 3:1.

11. The method according to claim 1, wherein said composition comprises a strain of bacteria *Lactobacillus reuteri* LRE03 DSM 23879 and a strain of bacteria *Lactobacillus salivarius* LS06 DSM 26037, in a weight ratio from 1:2 to 2:1.

12. The method according to claim 1, wherein said composition comprises a strain of bacteria *Lactobacillus reuteri* LRE03 DSM 23879 and a strain of bacteria *Lactobacillus salivarius* LS06 DSM 26037, in a weight ratio of 1:1.

13. The method according to claim 1, wherein said composition further comprises an *Aloe arborescens* gel.

14. The method according to claim 1, wherein said composition further comprises a freeze-dried *Aloe arborescens* gel.

15. The method according to claim 14, wherein the freeze-dried *Aloe arborescens* gel is in an amount from 5 to 15% by weight, relative to the weight of the composition.

16. The method according to claim 6, wherein said tyndallized bacterial product is in an amount of 20 mg/g of composition.

17. The method according to claim 1, wherein said composition further comprises fructooligosaccharides (FOS), green tea, sucralose and/or maltodextrins.

* * * * *